(12) United States Patent
Eason et al.

(10) Patent No.: US 6,226,962 B1
(45) Date of Patent: May 8, 2001

(54) CONTAINERS OF PARTICULATE MATERIAL

(75) Inventors: Stephen William Eason, Diss; Clive Patrick Ashley Catterall, Wantage; David Peter Griffin, Cambridge, all of (GB)

(73) Assignee: Lipha SA, Cedex (FR)

( * ) Notice: Subject to any disclaimer, the term of this patent is extended or adjusted under 35 U.S.C. 154(b) by 0 days.

(21) Appl. No.: 08/442,676

(22) Filed: May 17, 1995

(30) Foreign Application Priority Data

May 17, 1994 (GB) .................................................. 9409851

(51) Int. Cl.$^7$ ....................................................... B67B 5/00
(52) U.S. Cl. .................................................. 53/471; 53/281
(58) Field of Search ............................. 53/258, 281, 430, 53/453, 439, 467, 471, 473, 409, 204, 427; 141/67, 114, 325; 128/200.14, 203.15, 203.21; 221/31

(56) References Cited

U.S. PATENT DOCUMENTS

| | | | |
|---|---|---|---|
| 2,550,070 | * | 4/1951 | La Brecque et al. ................... 53/409 |
| 3,103,774 | * | 9/1963 | Wall ...................................... 53/427 |
| 3,208,192 | * | 9/1965 | Schaeffer .............................. 53/453 |
| 3,349,814 | * | 10/1967 | Webb .................................... 141/67 |
| 3,686,822 | * | 8/1972 | Wolfelsperger ........................ 53/427 |
| 4,219,987 | * | 9/1980 | Hannon ................................. 53/427 |
| 4,415,085 | * | 11/1983 | Clarke et al. .......................... 53/281 |
| 4,418,511 | * | 12/1983 | Collin ................................... 53/427 |
| 4,627,432 | * | 12/1986 | Newell et al. .................... 128/203.21 |
| 4,702,288 | * | 10/1987 | Ulveling et al. ....................... 141/67 |
| 4,733,449 | * | 3/1988 | Spearman ............................. 53/409 |
| 4,928,454 | * | 5/1990 | Bertolotti ............................. 53/409 |
| 4,955,412 | * | 9/1990 | Younts et al. ........................ 141/114 |
| 5,207,217 | * | 5/1993 | Cocozza et al. ................. 128/203.21 |
| 5,271,209 | * | 12/1993 | Boynham ............................. 53/539 |
| 5,617,971 | * | 4/1997 | Eason et al. ........................... 221/31 |
| 5,775,389 | * | 7/1998 | Griffin ................................ 141/325 |

\* cited by examiner

Primary Examiner—Peter Vo
Assistant Examiner—John Paradiso
(74) Attorney, Agent, or Firm—Lee, Mann, Smith, McWilliams, Sweeney & Ohlson

(57) ABSTRACT

A method of producing a container (201, 231, 350) having a plurality of apertures (eg 202, 232, 352) each containing a respective dose of powdered material, such as a medicament, involves placing an empty container in a position in which its apertures communicate with a reservoir (216, 84) of powdered material. The material is then passed, for example by the flow of gas, from the reservoir into the apertures to fill the latter, and the container is then separated from the reservoir and the apertures are optionally sealed with sheet material (204, 206, 321, 323). Since the apertures are filled, their volume determines the amount of each dose which therefore does not have to be measured prior to introduction into the apertures. The container may comprise a rigid or flexible plate and in latter case can be subsequently rolled into the form of a cylinder for use in an inhaler. Apparatus for performing the method, and an inhaler for use with a cylindrical container, are also shown.

13 Claims, 17 Drawing Sheets

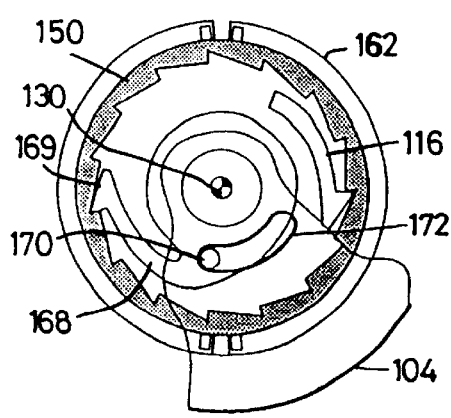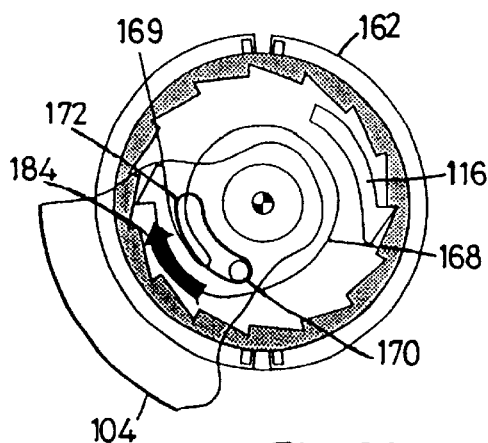
Fig.29A   Fig.29B
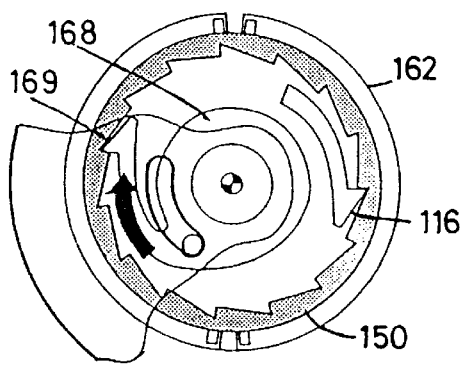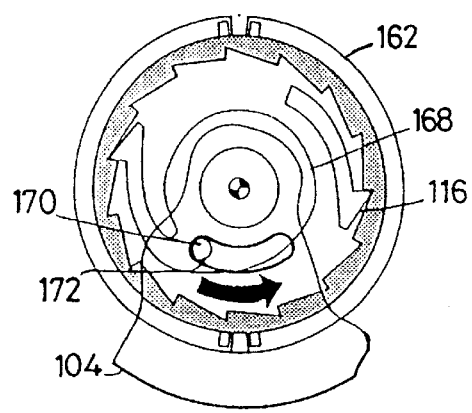
Fig.29C   Fig.29D
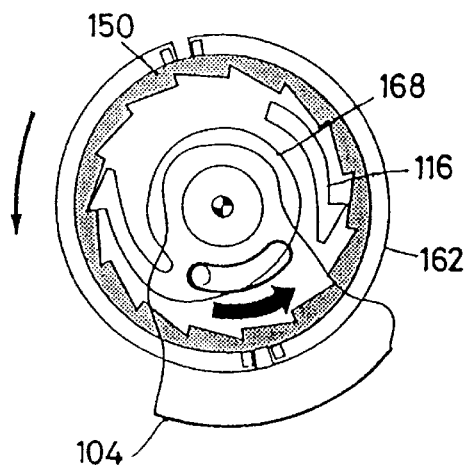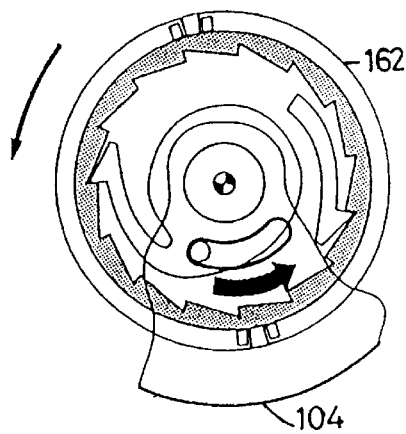
Fig.29E   Fig.29F

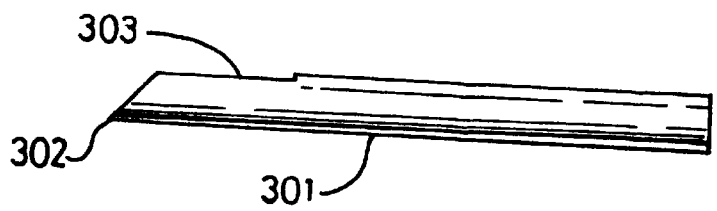
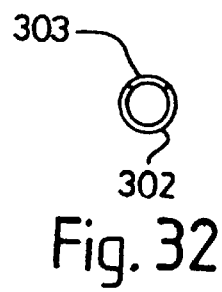
Fig. 31
Fig. 32
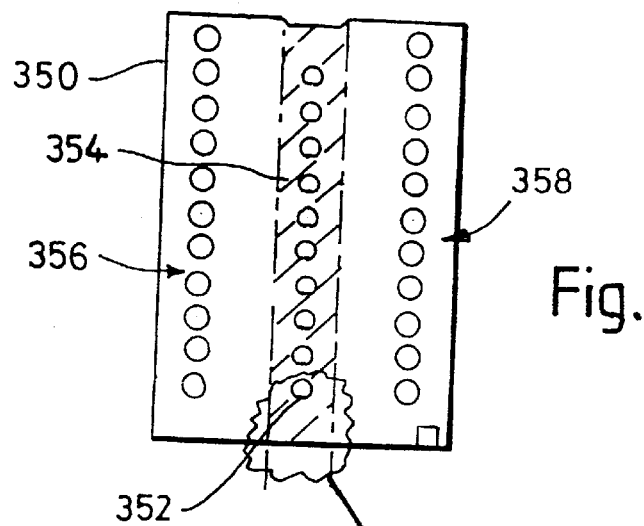
Fig. 33
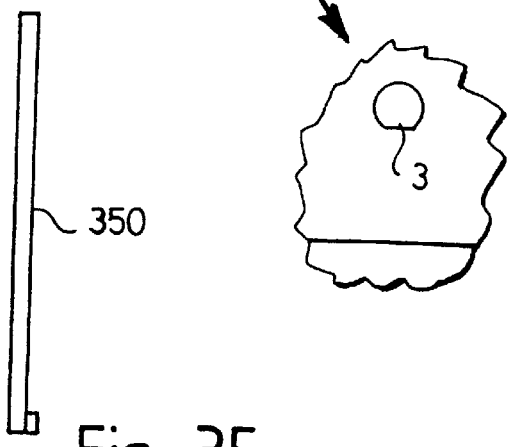
Fig. 34
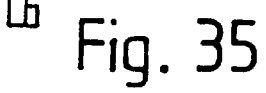
Fig. 35

CONTAINERS OF PARTICULATE MATERIAL

FIELD OF THE INVENTION

The invention relates to a method of providing a container and a plurality of individual doses of particulate material, particularly powdered medicament, contained therein, and to apparatus for performing the method. The invention is of particular application to devices for administering single doses of powdered medicament by inhalation.

BACKGROUND TO THE INVENTION

It is known to provide a pharmacologically active compound in finely divided particulate form for self administration by inhalation to relieve respiratory problems, particularly asthma.

Such compounds can be provided in containers, each of which has a number of compartments, each containing a respective dose of the compound. Such containers are used in conjunction with an inhaler which releases each dose of the compound in turn. For example, European Patent specification No EPO 211595 (Glaxo Group Limited) shows an inhaler in which particular material is administered from a disc-shaped blister pack.

The blisters of the disc are loaded with powder by means of a filling head which separates individual doses of compound from a reservoir and allows those doses to pour into the blisters. The inherent inaccuracies in the measurement of each dose, and the need to provide a powder with suitable flow characteristics to enable filling result in the compound having to be mixed with a significant amount of lactose.

This increases the required size of the individual blisters in the container, thus reducing the number of doses which can be dispensed from a container of a given size. In addition, the user, in self administering a dose of medicament, has to inhale a relatively large amount of powder which can give rise to an unpleasant sensation in the user's mouth and throat.

SUMMARY OF THE INVENTION

According to a first aspect of the invention, there is provided a method of loading a container having a plurality of compartments, with a plurality of doses of a predetermined amount of particulate material, the method comprising the steps of:
1. bringing each compartment into a position in which it communicates with a reservoir of an excess amount of the particulate material;
2. causing the material to enter and fill the compartments; and
3. separating the compartments from the reservoir, wherein each compartment contains a respective dose and the volume of each compartment determines the amount of dose contained therein.

Preferably, the particulate material is a powdered medicament which may to advantage be of a type which is self administered by inhalation using an inhaler.

Since each dose of material is effectively metered by the compartments in the container, the need for measuring the doses before filling the container is avoided, the amount of material in each compartment is more accurately controlled, and the need for any substantial amount of additional material, such as lactose, is reduced or avoided. Consequently, the container can be configured to hold a relatively large number of doses, and the user does not have to inhale a large amount of particulate material when self administering one such dose.

Preferably, the container comprises a plate and each compartment comprises a respective aperture therein.

Preferably, the compartments are all simultaneously brought into a position in which they communicate with a common reservoir.

Preferably the particulate material is drawn into the apertures by passing a gas through the particulate material in the reservoir and the apertures.

The use of gas provides additional control over the force with which the particulate material is urged into the apertures, and hence the density of the material therein.

Preferably, before the particulate material is applied, the plate is placed on a porous bed beneath the reservoir, which bed allows the passage of said gas therethrough, whilst preventing particulate material from passing all the way through the apertures and escaping from the underside of the plate.

Preferably, the bed comprises a perforated base plate and a sheet of finely porous material, for example filter paper, interposed, in use, between the base plate and the container.

The apertures, once filled, are preferably sealed so that each dose is individually encapsulated in its respective aperture, and said sealing is conveniently achieved by bonding a respective sheet of material to each face of the plate.

Preferably, the sheet material which seals the apertures comprises a laminated foil which is attached to the body by being heat sealed thereto.

The laminated foil tends to resist any tendency for fragments of the sheet to be broken off the rest of the sheet when the seal for a given compartment is ruptured to allow material to be discharged from that compartment.

The plate may be flexible, in which case the method preferably includes the steps of rolling or otherwise forming the plate into a cylinder once it has been filled.

The container may be retained in its cylindrical configuration by applying an annular end cap thereto, typically two said end caps are used one at each end.

Such a plate preferably comprises an array of elongated flat, substantially rigid strips, adjacent pairs of which are hingeable relative to each other, such that the strips are substantially parallel to the axis of the cylinder in the finished container.

Alternatively, the plate can constitute one of a number of strips which are fitted together to form a cylindrical composite container.

Preferably, the reservoir is contained in a hopper having an array of outlet holes, each of which is in registry with a respective aperture when the apertures are in said position relative to the reservoir, and said gas is supplied to the hopper under sufficient pressure for the particulate material to pass through the outlet holes and into the apertures.

Preferably, the dimensions of the outlet holes are such that substantially none of the particulate material passes therethrough when gas is not being supplied to the hopper.

Thus, by interrupting the supply of gas to the hopper, it is possible to remove the plate therefrom without any substantial amount of particulate material being lost from the bottom of the hopper.

According to a second aspect of the invention, apparatus for performing the method of the first aspect of the invention comprises a porous bed on which the plate can be laid out flat; a filling head for supplying particulate material to the upper surface of the plate and means for moving air or a gas through the bed and the apertures in the plate to draw particulate material thereinto.

Preferably, the filling head comprises a hopper having a series of outlet holes, the relative positions of which correspond to those of the aperture in the plate so that, with the plate in position under the hopper, each hole is in registry with a respective aperture.

Preferably, the apparatus includes level detection means for determining the level of particulate material remaining in the hopper, and supply means for supplying further particulate material thereto.

If the hopper is elongate, the supply means and level detection means are preferably so arranged that material is supplied to one end of the hopper, and the level detection means detects the level of the material at the opposite end of the hopper, the apparatus including distribution means for levelling the particulate material in the hopper.

The invention also lies in a method of making a cylindrical body having a plurality of compartments, each containing a respective dose of material, the method comprising the steps of:

(1) applying particulate material to one face of each of a plurality of elongate substantially flat members, each said member having a plurality of compartments accessible from said face;
(2) causing the particulate material to enter said compartments;
(3) joining the members together to form a composite member consisting of said elongate members positioned side by side; and
(4) rolling, or otherwise forming, the composite member into a generally cylindrical form in which each said elongate member extends along the length of the body.

BRIEF DESCRIPTION OF THE DRAWINGS

The invention will now be described, by way of example only, with reference to the accompanying drawings in which:

FIGS. 29A–29F are diagrammatic sectional views illustrating the operation of part of the inhaler, at various stages during its cycle of operation;

FIG. 31 is a side view of a component of the inhaler;

FIG. 32 is an end view of that component;

FIG. 33 shows from the front an alternative type of container which can also be filled by a method in accordance with the invention;

FIG. 34 shows a detail of that container; and

FIG. 35 is a side view of that container.

DETAILED DESCRIPTION

With reference to FIGS. 1A–1H, a container comprises a body 201 which includes a number of through-bores, eg 2, for containing a respective dose of medicament. For the sake of clarity, the body illustrated in FIGS. 1A–1H has only 16 such through bores, although in practice a larger number of through bores may be present in the body 201.

In the finished container, the body 201 is of a generally cylindrical shape, and the bores are radially disposed, and are sealed by an outer sheet 204 and an inner sheet 206 of laminated foil heat sealed to the body 201.

Figure 1A:
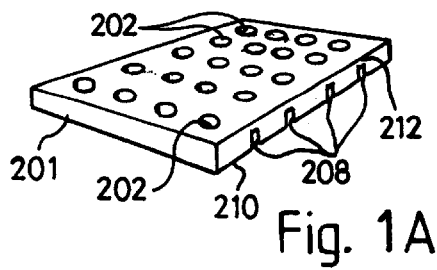
FIGS. 1A–1H are simplified diagrams showing various stages of a method, in accordance with the invention, of making a cylindrical container.
Figure 1B:
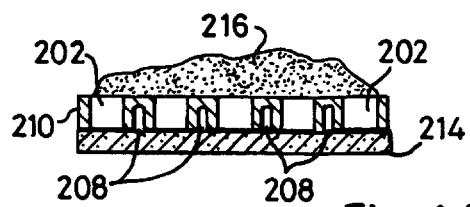

With reference to FIG. 1A, the body 201 comprises a rectangular plate of a plastics material, the underside of which includes a number of grooves 208 arranged in a regular parallel array. The grooves 208 divide the member into a number of parallel rigid strips, such as strip 210 running across the width of the plate. Adjacent pairs of strips are connected by corresponding reduced thickness-portions, such as portion 12. The thickness of the plastics material constituting those portions is such that the adjacent strips are hingeable relative to each other. The through bores in the body 201 are all provided in the strips.

The plate 201 is laid flat on a bed 214 of a porous material, with the non grooved face of the body upper most, and the upper surface of the plate 201 is covered with a layer of powdered medicament 216, which covers one end of each of the through bores.

Figure 1C:
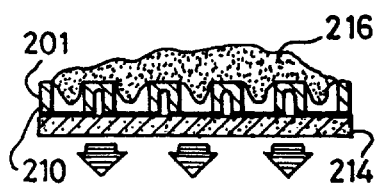

With reference to FIG. 1C, nitrogen is then passed down through the layer 216 of the through bores through the bed 214, causing the material 216 to pass into each of the through bores. The porosity of the bed 214 is such that it is impervious to the material 216. As a result, the bed 214 prevents material 216 being discharged from the bottom of the through bores.

Figure 1D:
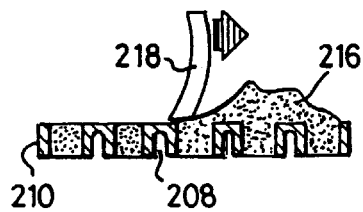
Figure 1E:
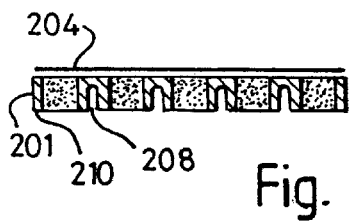
Figure 1F:
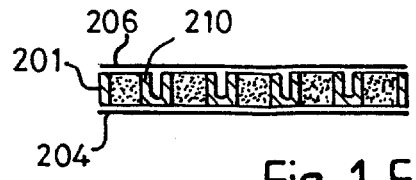
Figure 1G:
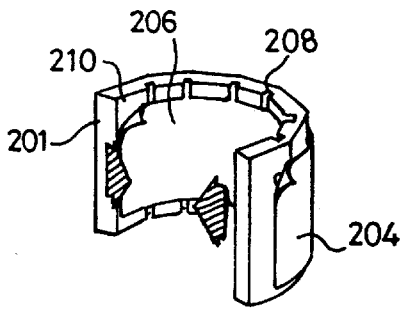
Figure 1H:
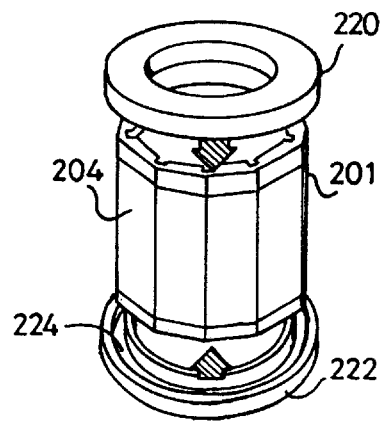

When the through bores have been filled with the material 216, any excess material which has not been drawn into a through bore is removed by drawing a resiliently flexible blade 218 across the upper surface of the plate 201 (FIG. 1D). The sheet 204 is then heat sealed onto the upper surface of the plate 1 (FIG. 1E), which is then inverted so that the sheet 206 can be similarly applied to the opposite face of the plate 1 (FIG. 1F).

The flexibility provided by the reduced thickness portions between the strips of the plate 201 enable the latter to be rolled (FIG. 1G) into a generally cylindrical shape, with the strips extending axially along the cylinder, and the grooves 208 on the inner surface thereof.

Two ring-shaped end caps 220 and 222 are then attached one at each end of the cylinder. Each cap includes an annular track, eg track 224, into which the strips extend and in which the strips are a tight fit. Thus the caps 220 and 222 prevent the cylinder from unravelling. The components shown in FIGS. 2A–2E correspond with those shown in FIGS. 1A–H, and corresponding components are indicated by the same reference number raised by 30. Thus the container comprises a body 231 which is formed by rolling a plate (also referenced 231), and which has a number of through-bores eg 232 which are filled with powdered medicament by means of the same method as illustrated in FIG. 1, and are sealed on one side by a first sheet of laminated foil 234 and on the other side by a second sheet of laminated foil 236 applied to the plate 231 after it has been inverted.

It will be seen that the body 231 contains a larger number of through-bores, eg 232, than the body 1, and can therefore contain a greater number of doses of medicament than the body 201. In addition each of the grooves in the plate 231, eg groove 238, is tapered so as to facilitate rolling. The caps 250 and 252 each include diametrically opposed inner slot arrangements, for example 256 and 258 which enable the container to be rotationally keyed to the rotational core or an inhaler in which the container is to be used.

Figure 2A:
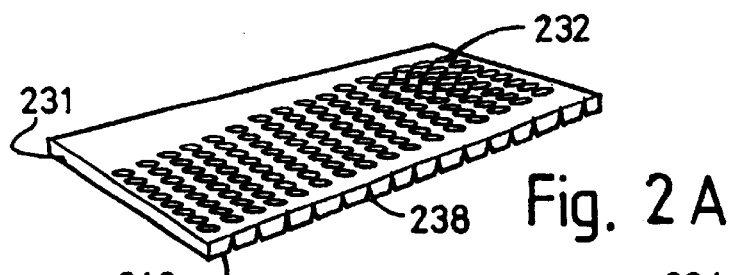
FIGS. 2A–2E show components of an alternative type of cylindrical container which can be filled by the method illustrated in FIGS. 1A–H, FIG. 2E showing the container when assembled.
Figure 2B:
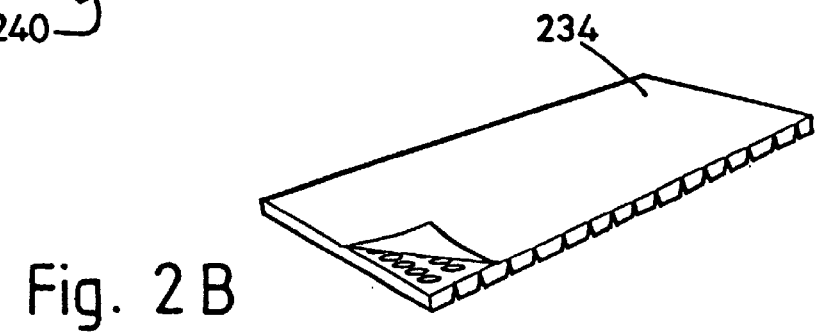
Figure 2C:
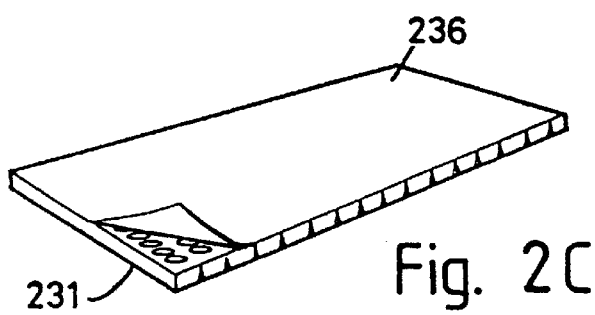
Figure 2D:
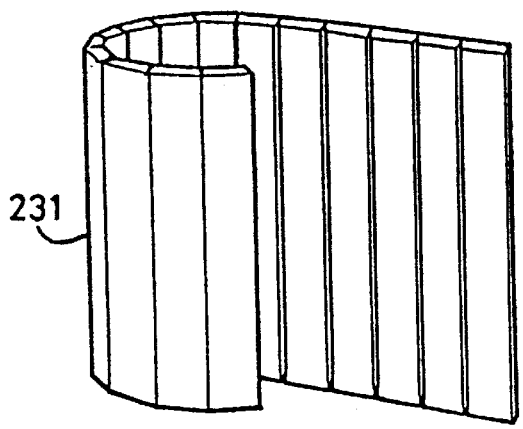
Figure 2E:
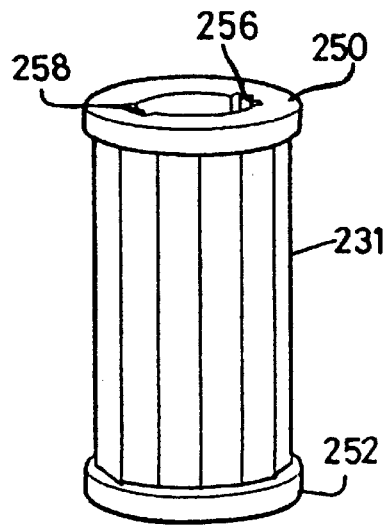

As can be seen from FIG. 2A, the through-bores are so arranged as to lie on a helical path on the body 31, when the container is assembled.

Figure 3:
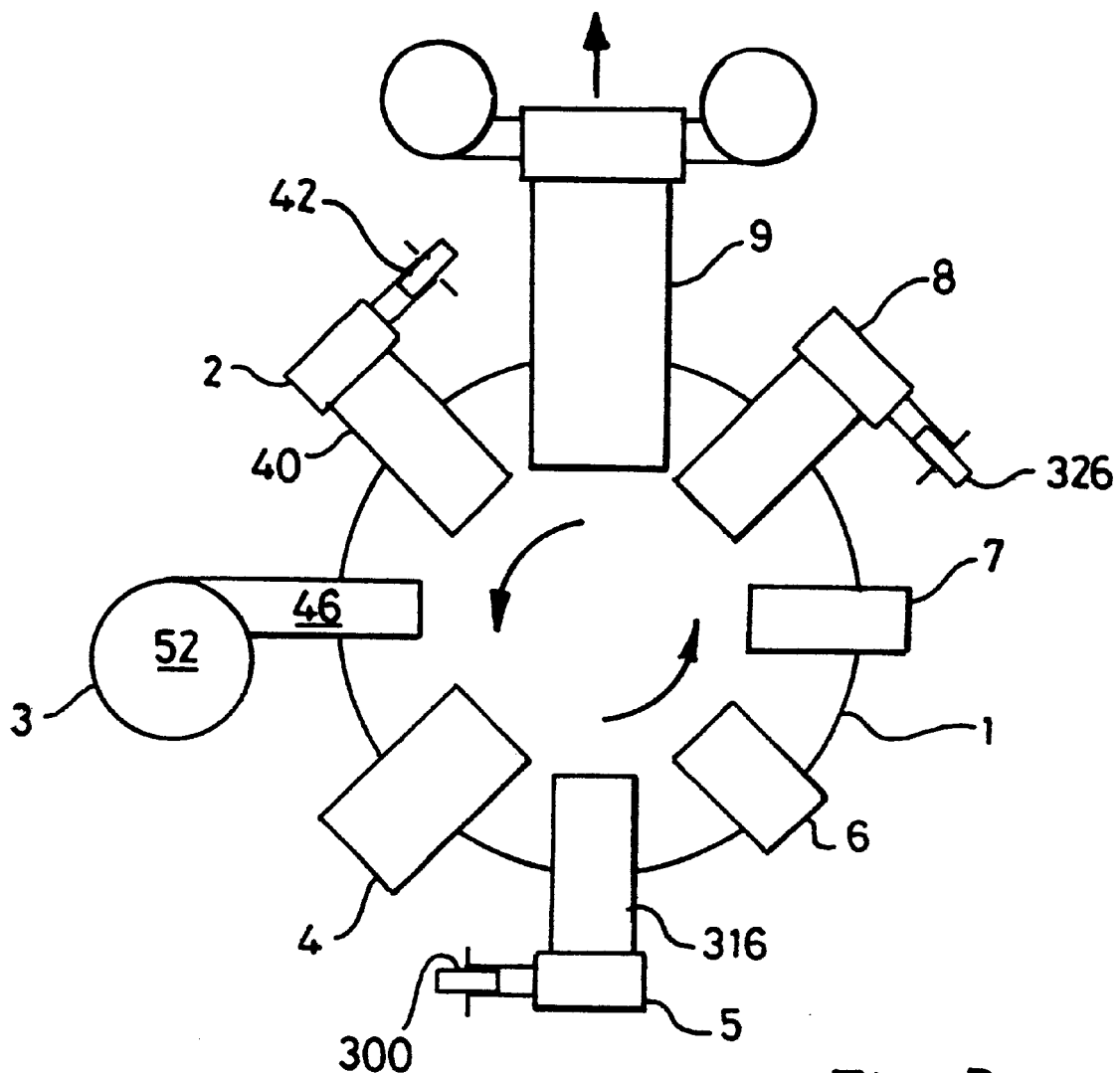
FIG. 3 is a plan view of the apparatus for performing a modified version of the method, the apparatus having a number of stations, arranged around the carousel, at which various steps are performed.

The apparatus shown in FIG. 3 comprises a carousel 1 and eight stations 2–9 positioned around the periphery thereof. In use, the carousel rotates in an anti-clockwise direction to transport components on the carousel to each of the stations in turn, as described below.

Figure 4:
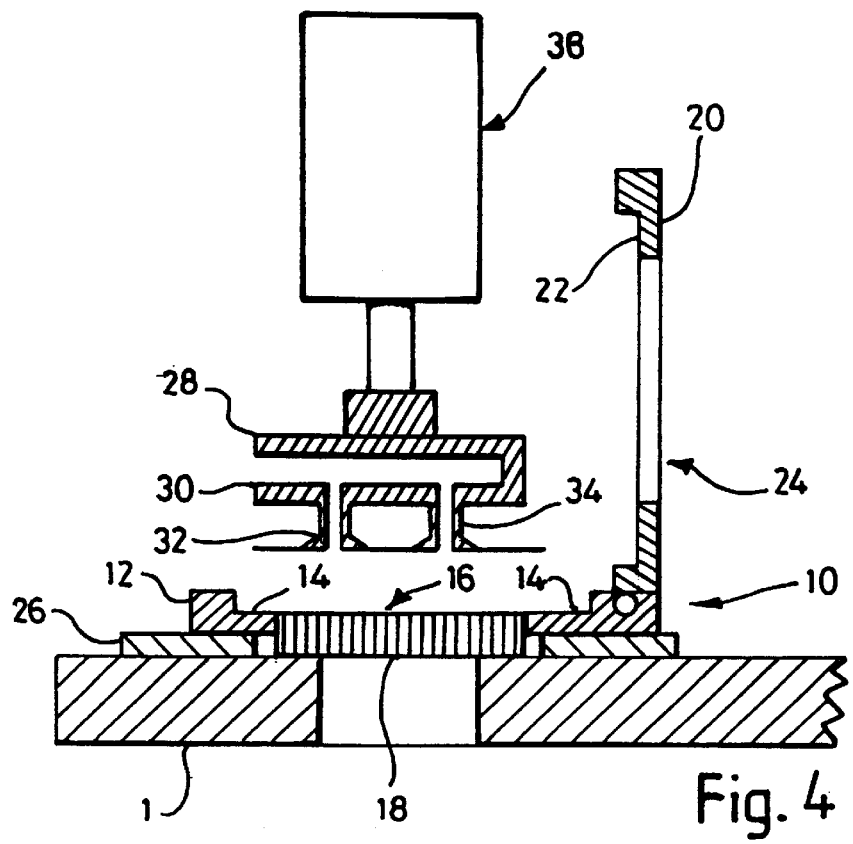
FIG. 4 is a diagrammatic sectional view taken in a radial plane, of the first of said stations.

With reference to FIG. 4, the apparatus includes a holder 10 for releasably retaining a container in the form of a rectangular plate. The holder 10 has a first rectangular frame portion 12 having an inner peripheral rectangular flange 14 which bounds a rectangular central opening 16. That gap accommodates a perforated metal block 18. The holder 10 also includes a second rectangular frame 20 which is pivotally mounted on the frame 12, and which also has a peripheral flange 22 and a central aperture 24. The holder 10 is releasably attached to the carousel 1 through an apertured plate 26.

As can be seen from FIG. 4, the station 2 includes a block 28 which has a central passage 30 which communicates with two feet 32 and 34. The passage 30 is selectably connected to a source of vacuum, and the block 28 is mounted on a pneumatic piston and cylinder assembly 38 which is operable to raise and lower the block 28. The piston and cylinder assembly 38 is, in turn, suspended from an upper plate 40 (FIG. 3) through drive means (not shown) operable to move the assembly 38, and hence the block 28, radially.

A reel 42 of filter paper is provided at the radial outer end of the station 2, which includes a punch and die mechanism (not shown) for cutting the filter paper to length.

The block 28, in use, retrieves a cut-out for filter paper from the radial outer end of the station 2, a vacuum being applied to the passage 30 to retain the cut-out on the feet 32 and 34, conveys it radially inwards to the position shown in FIG. 4, and then lowers the filter paper onto the block 18. The vacuum is then disconnected so that when the block is raised, the filter paper remains in the holder 10.

Figure 5:
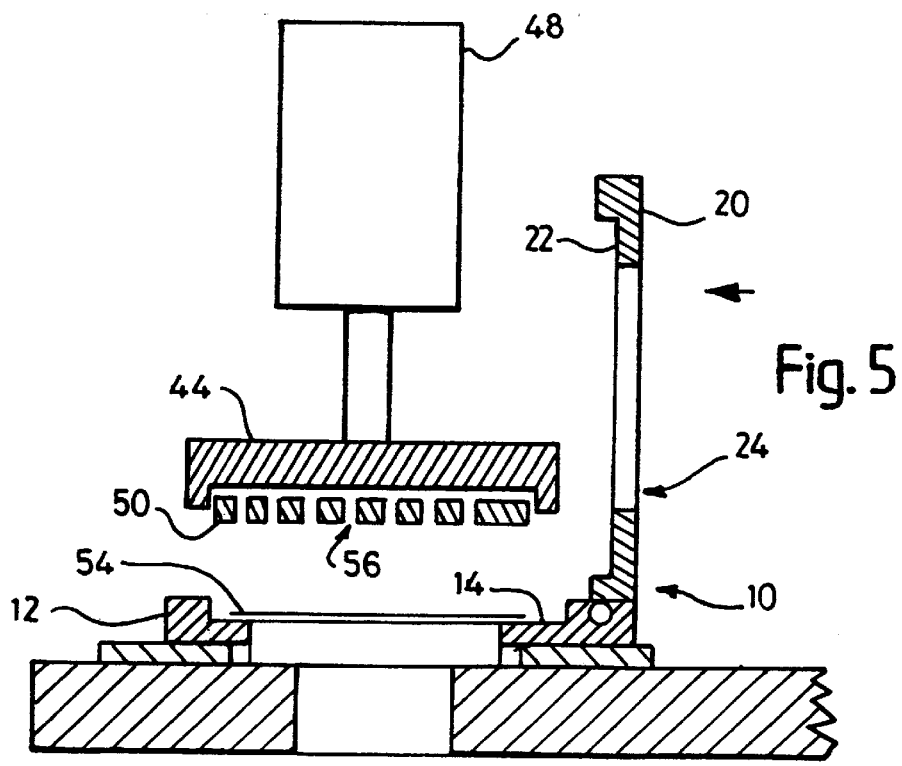
FIG. 5 is a diagrammatic sectional view, taken in a radial plane, illustrating a second of said stations and the steps carried out thereat.

The holder 10 is then conveyed on the carousel 1 to the station 3, which is shown in more detail in FIG. 5. The station 3 has a pneumatic gripper 44 which is mounted on an upper plate 46 through a pneumatic piston and cylinder assembly 48, which, in turn, can be radially moved by drive means (not shown). In use, the gripper 44 collects a container 50 from a magazine 52 at the radial outer end of the station 3, conveys the container 50 to the position shown in FIG. 5 and places it in the holder 10 on the filter paper (referenced 54). The gripper 44 is then removed and the frame 20 is lowered onto the frame 12 so that the filter paper 54 and container 50 are clamped between the flanges 14 and 22. The container 50 comprises a flexible plate having an array of apertures, one of which is referenced 56. The container is similar to the containers shown in FIGS. 1A and 2A.

Figure 6:
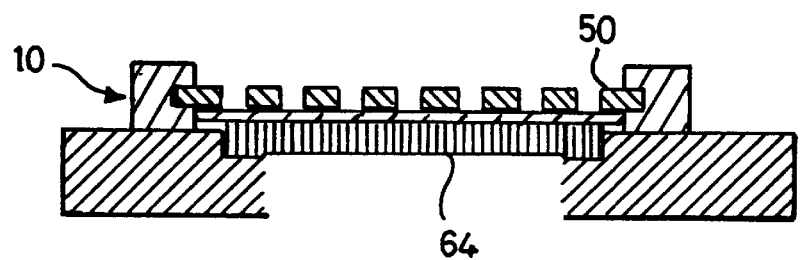
FIG. 6 is a similar view of elements which are transported along the carousel from the second to the third station.
Figure 7:
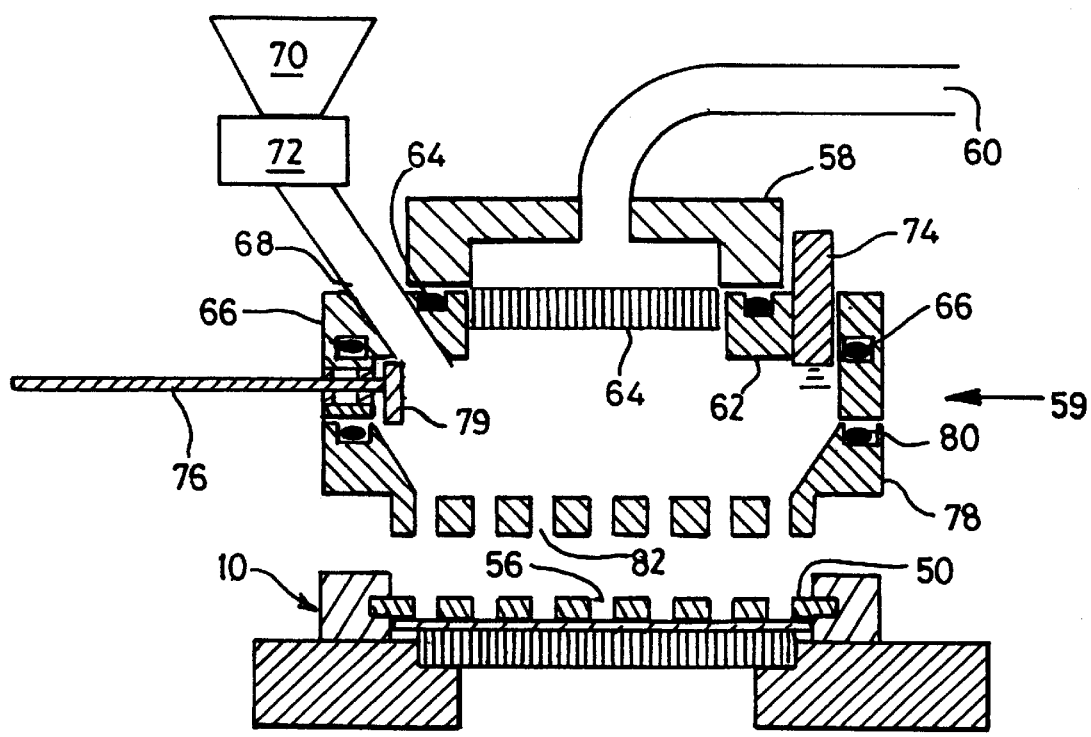
FIGS. 7–11 are radial sectional views of the third station at various stages of its operation.
Figure 8:
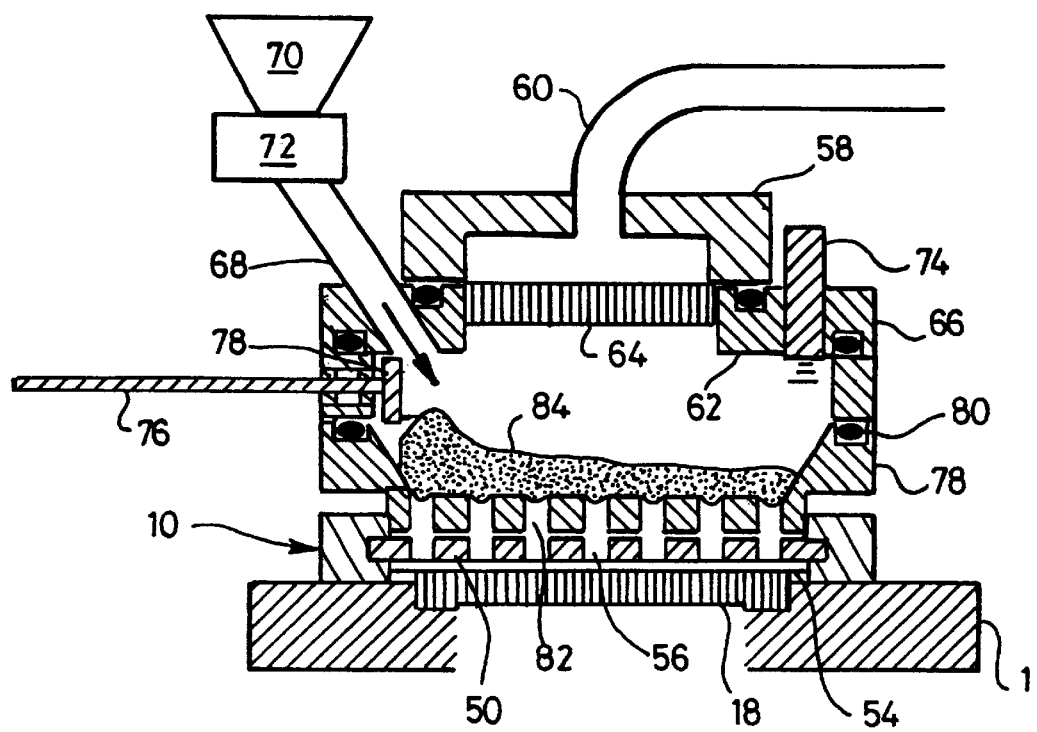
Figure 9:
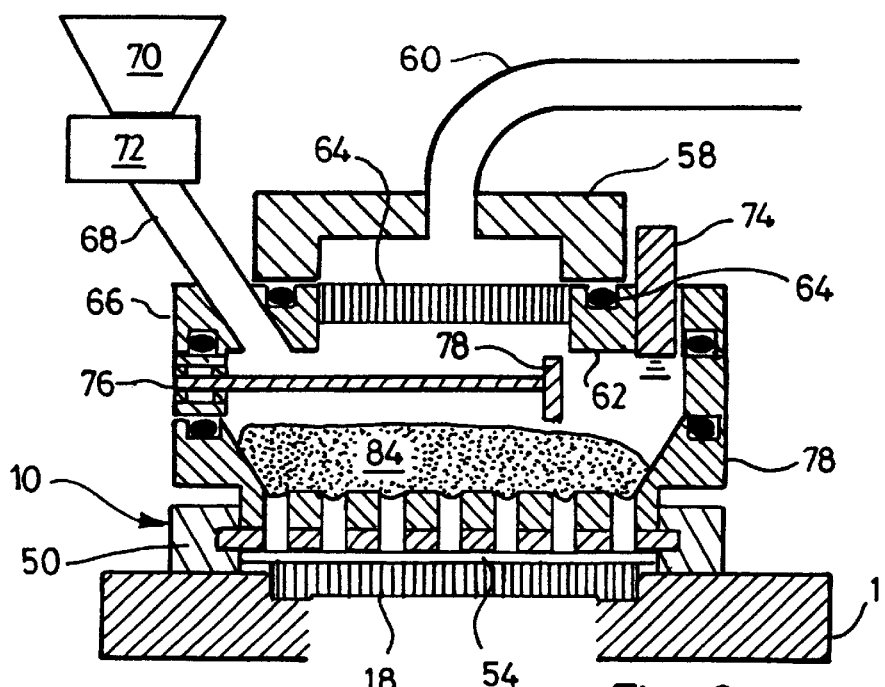

The holder, with the container and filter paper retained therein (as shown in FIG. 6), is then transported to the filling station 4 which is shown in FIG. 7. In FIGS. 6 to 21, the holder 10 is shown in a simplified form, for the sake of clarity.

The filling station 4 comprises a filling head 59 having a rectangular inlet manifold 58 which communicates with a pipe 60 through which pressurised nitrogen can be selectively supplied to the manifold. The manifold 58 is sealed against a rectangular upper frame portion 62 by an o-ring seal 64. The portion 62 includes a central rectangular opening which accommodates a diffuser 64 in the form of a perforated block, a peripheral rectangular frame portion 66 surrounds the portion 62, and defines, with the portion 62, a first end aperture which accommodates an inlet chute 68, along which powdered medicament is supplied, in use, from an auger 70 via valve 72. The frames 62 and 66 also define an aperture opposite said chute 68 for accommodating an ultrasonic level sensor 74. The peripheral frame includes a further aperture in one side thereof through which a rod 76 extends. The end of the rod is attached to a rectangular plate 79, the elongate axis of which extends substantially perpendicular to the plane of FIG. 7.

A hopper 78 is sealed against the base of the frame 66 to an o-ring seal 80. The bottom of the hopper 78 includes a linear array of holes, one of which is denoted 82 which are in positions corresponding to the positions of the apertures in the container 50. The assembly positioned above the holder 10 in container 50 can be lowered into the position shown in FIG. 9, in which the bottom of the hopper 78 closely abuts the contained 50, and the holes in the hopper 78 register with the apertures in the container 50.

Powdered medicament 84 is then introduced into the hopper through the chute 68. The detector 74 then senses the level of the medicament 84 at the end of the hopper opposite the chute 68, and if that level is insufficient, the rod 76 is extended, causing the plate 79 to redistribute the medicament 84 over the holes in the hopper.

Nitrogen is then introduced through the pipe 60, and passes through the diffuser 64 (which prevents the flow of nitrogen adversely affecting the distribution of the particulate material 84) through the material 84, the holes in the bottom of the hopper 78 and through the apertures in the container 50. Nitrogen exiting the apertures in the container 50 passes through the block 18 via the filter paper 54. This passage of nitrogen urges the powdered medicament 84 through the holes in the hopper 78 and into the apertures in the container 50, whilst the filter paper 54 prevents the powdered medicament being expelled through the bottom of the apertures.

Figure 12:
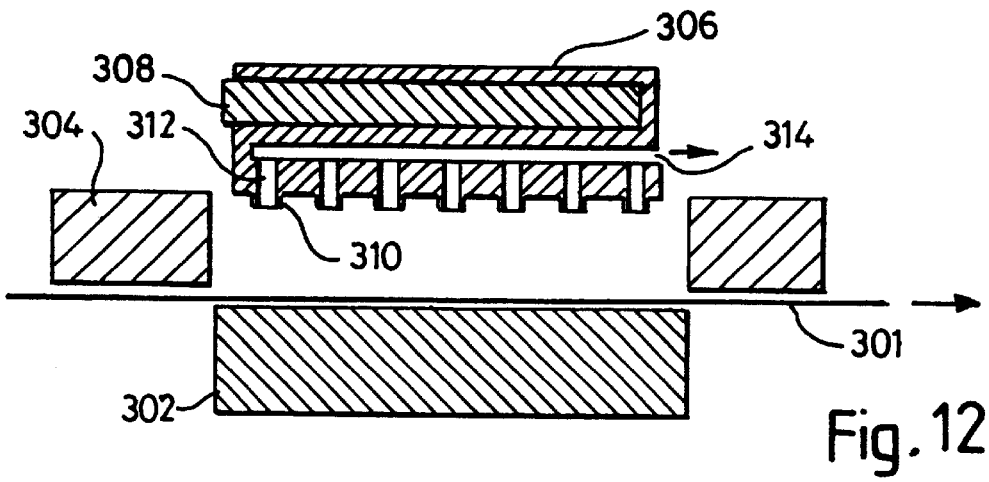
FIGS. 12–16 are radial sections of parts of the fourth station at various stages in its operation.

The filling head 59 is then raised from the container 50 as shown in FIG. 12, and a further charge of powdered medicament is poured into the hopper for the next filling, and if necessary levelled by the plate 79. The filled container 50 and its holder 10 are then transported by the carousel 1 to the station 5 which includes, at its radial outer end, a reel 300 of a web 302 of foil laminate, and feed-means (not shown) for feeding foil from the reel past a punch 302 and a die 304, which die defines a rectangular aperture. A sealing head 306 is mounted at the same end of the station 5, in registry with the aperture defined by the die 304 by means of a pneumatic piston and cylinder assembly (not shown) which is operable to raise and lower the head 306.

The head 306 includes a heater 308 and a number of feet, one of which is referenced 310, arranged in a rectangular array at the underside of the head 306. Each foot is in the form of a short hollow cylinder, the interior of which communicates with a vertical passage, for example 312. The vertical passages, in turn, communicate with a horizontal common passage 314 which is selectively connectable to a vacuum source (not shown).

Figure 13:
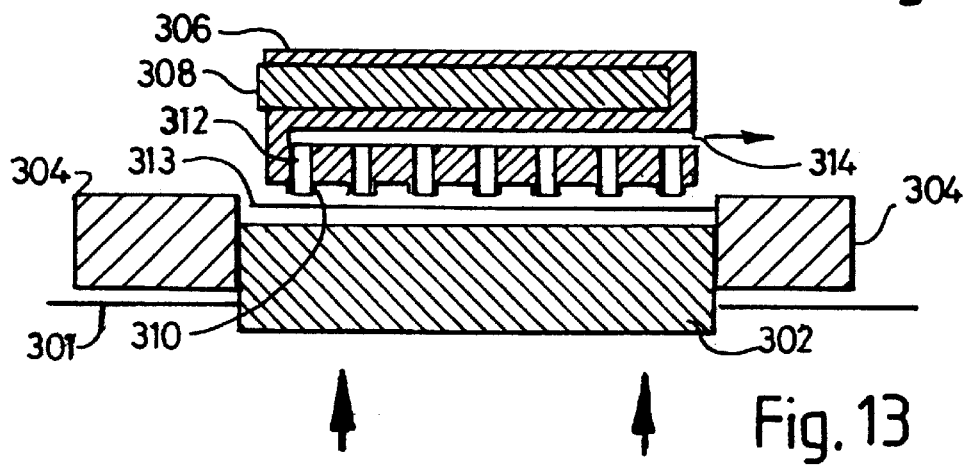
Figure 14:
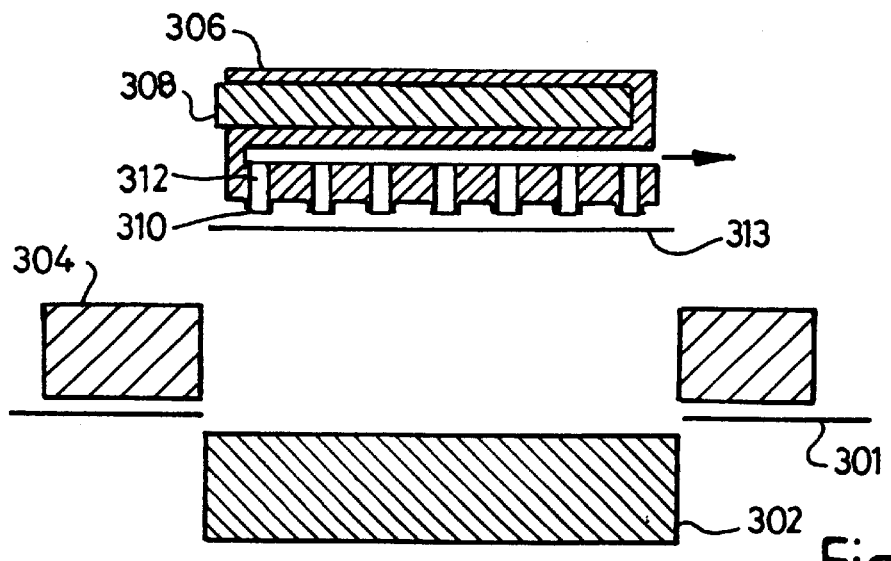
Figure 15:
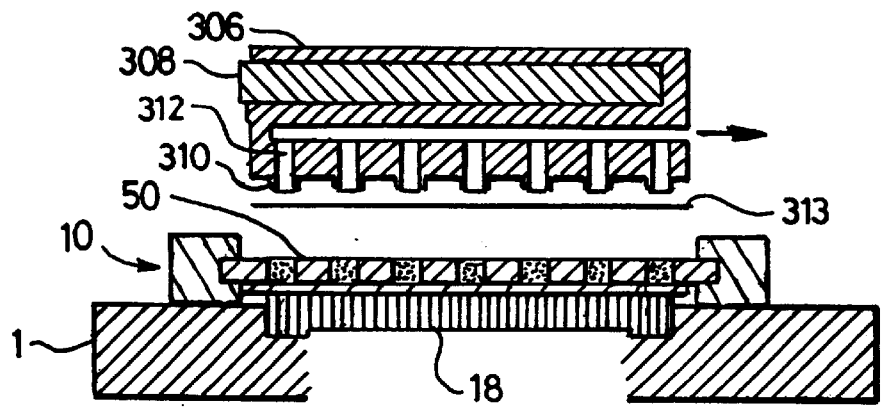

With reference to FIG. 13, the punch 302 is al so mounted on a pneumatic piston cylinder arrangement (not shown) which is operable to raise the punch 302, causing it to cut from the length of foil 301 a rectangular piece 313 which is moved up into contact with the head 306. As this happens, the passage 314 is connected to the vacuum source which causes the feet on the head 306 to hold the piece 313 thereon.

The web of foil 301 is wider than the cut-out 313, and as a result, when the punch 302 is returned to the position shown in FIG. 13, a fresh piece of foil can be drawn into position above the punch 302 by means of a reel assembly (not shown) positioned to the right of the components shown in FIG. 12, which is on the opposite side of those components from the reel 300.

The piston and cylinder assembly on which the head 306 is mounted is mounted on a top plate 316 (FIG. 3) via a drive mechanism for moving the head 306 in either radial direction. Thus, once the cut-out 313 has been attached to the head 306, the latter is raised into the position shown in FIG. 15 and the drive means operates to move the head radially inwards into the position shown in FIG. 16, in which it is positioned above the container 50.

Figure 16:
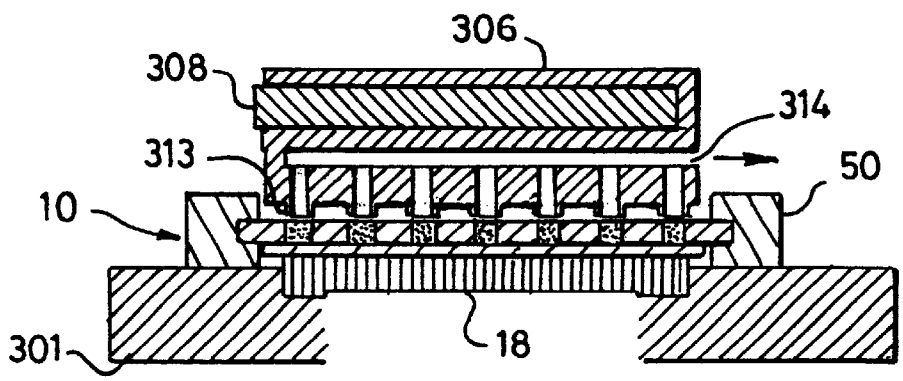

The head 306 is then lowered onto the container 50 as shown in FIG. 16. The foil laminate of the cut-out 313 has an upper layer (in contact with the feet on the head 306) which is substantially unaffected by the heat from the heater. However, the lowermost layer of the laminate is partially fused by the heat from the heater 308, causing the cut-out 313 to be heat-sealed to the container 50. The passage 314 is then disconnected from the vacuum supply, and the head 306 is raised and returned to the position shown in FIG. 12, leaving the contained 50 with a foil laminate seal on one face.

Figure 17:
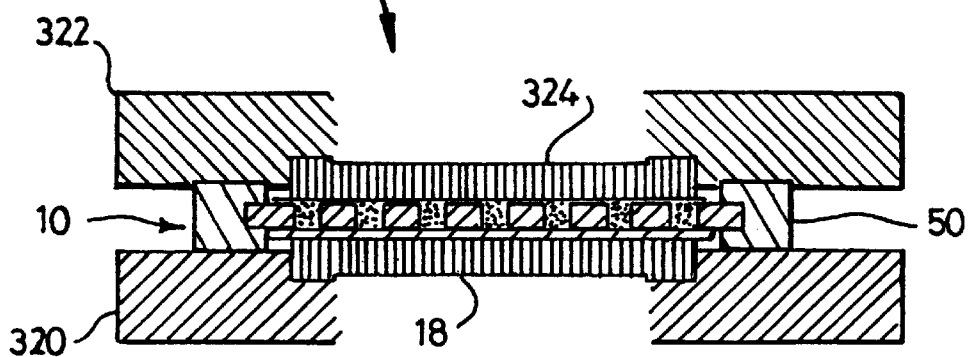
FIGS. 17 and 18 are similar views of the fifth of said stations.
Figure 18:
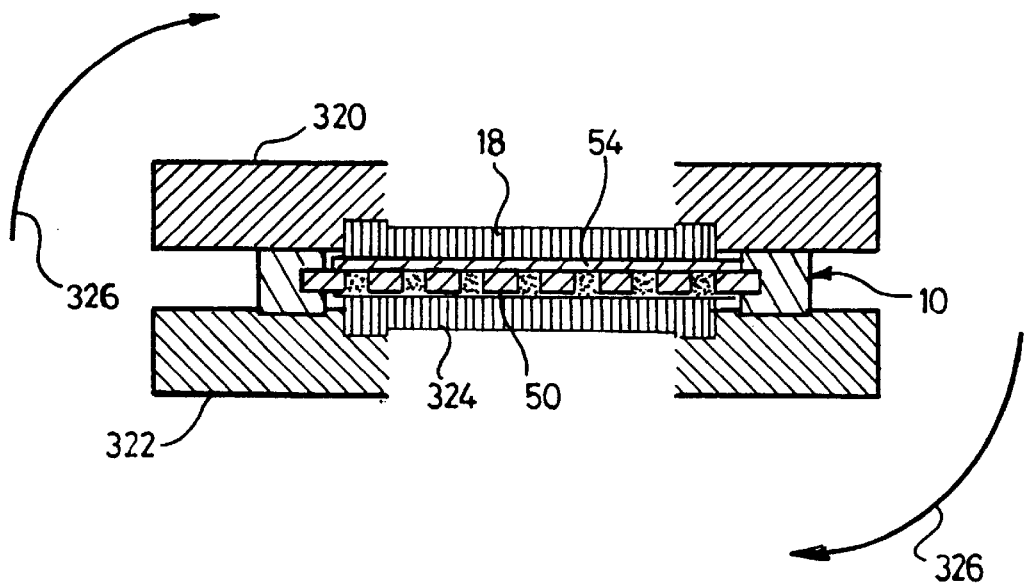

With reference to FIG. 17, the container 50 and its holder 10 are then transported to the station 6 at which the container 50, the support 10 and the plate 18 are removed from the carousel 1 and placed on a support block 320. A similar support block 322 and perforated plate 324 are then placed on top of the container 50 and holder 10. The supports 320 and 322 are connected to a mechanism (not shown) which inverts the elements shown in FIG. 17 in the way indicated by the arrows 326 in FIG. 18 so that the block 320 is then uppermost. The components shown in FIG. 18 are then transported to the station 7 which includes a head (not shown) which releasably grips the top of the support 320 and which has a suction mechanism which seals against the plate 324, to cause the filter paper 54 to be held against the plate 18. The head is then moved away from the container 50, taking the block 320, the plate 18 and the paper 54 with it, as shown in FIG. 19.

Figure 19:
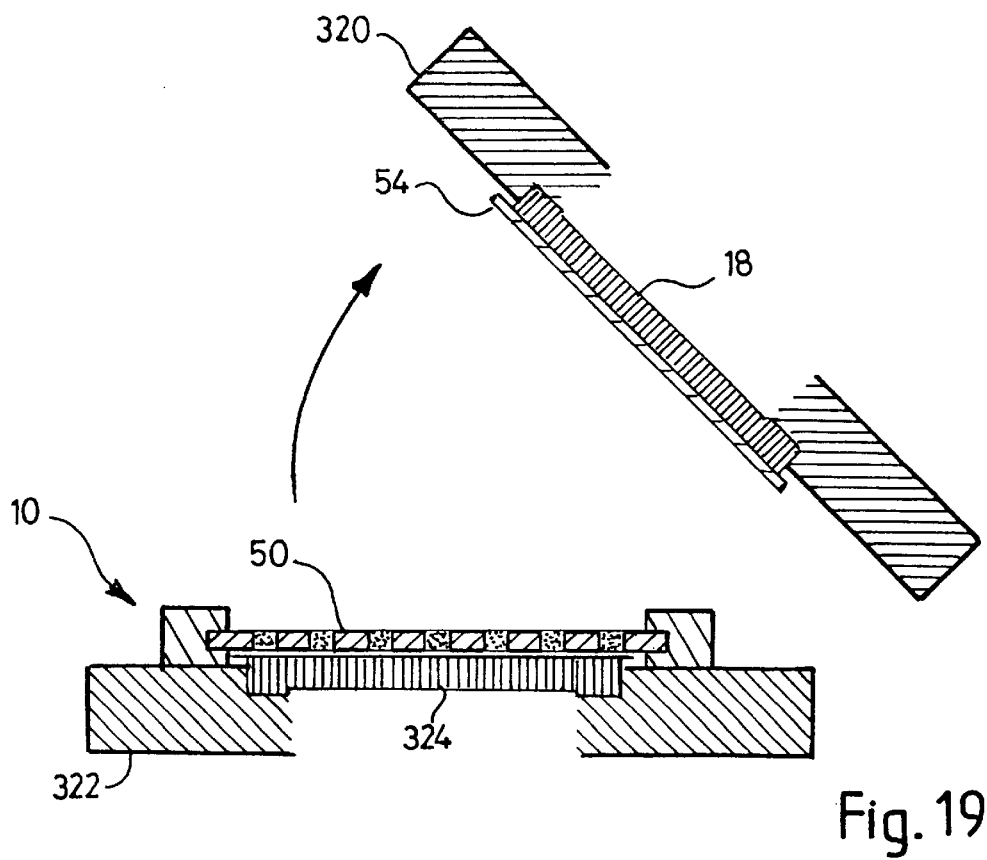
FIG. 19 is a similar view of the sixth station
Figure 20:
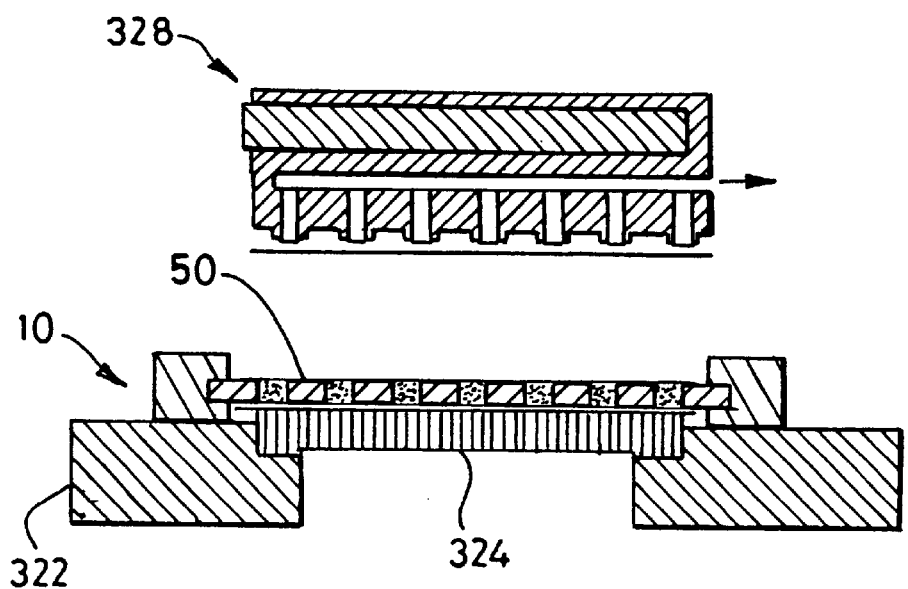
FIG. 20 shows parts of the seventh station.

The remaining elements shown in FIG. 19 are then transported to the station 8 which is similar in form and function to the station 5, and which thus includes a reel 326 of foil laminate which is fed to a punch and die assembly similar to the punch and die 304 and 302. The punch and die cut out a piece of the foil laminate which is then applied to a head 328 of the same kind as the head 306. The head 328 is mounted at the station 7 by a similar arrangement used to mount the head 306 on the station 5, so that the head 328 can move radially into the position shown in FIG. 20 in which is is directly above the container 50. The head is then lowered, sealing the cut out piece of foil laminate to the container 50.

Figure 21:
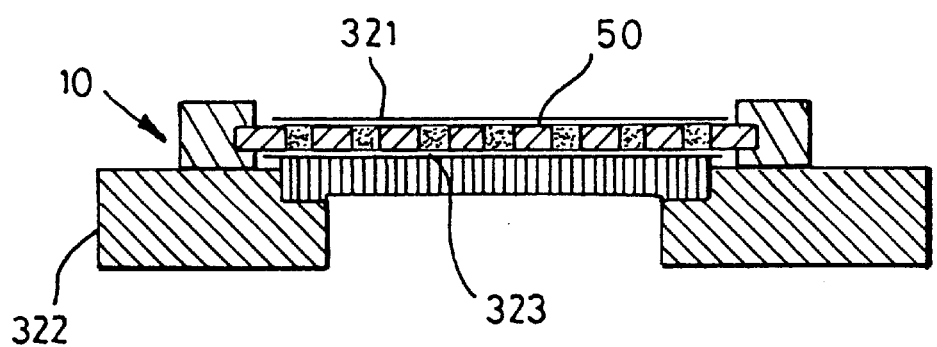
FIG. 21 shows the elements which are transported from the seventh station to the eighth station.

FIG. 21 shows the container 50 in its filled and sealed form, still in its holder 10. The sheets of foil laminate are referenced 321 and 323. In this form, the container 50 an d holder 10 are fed to the station 9 at which the container 50 is removed from the holder 10 and rolled into the form of a cylinder in a similar fashion to the method previously described.

Figure 22:
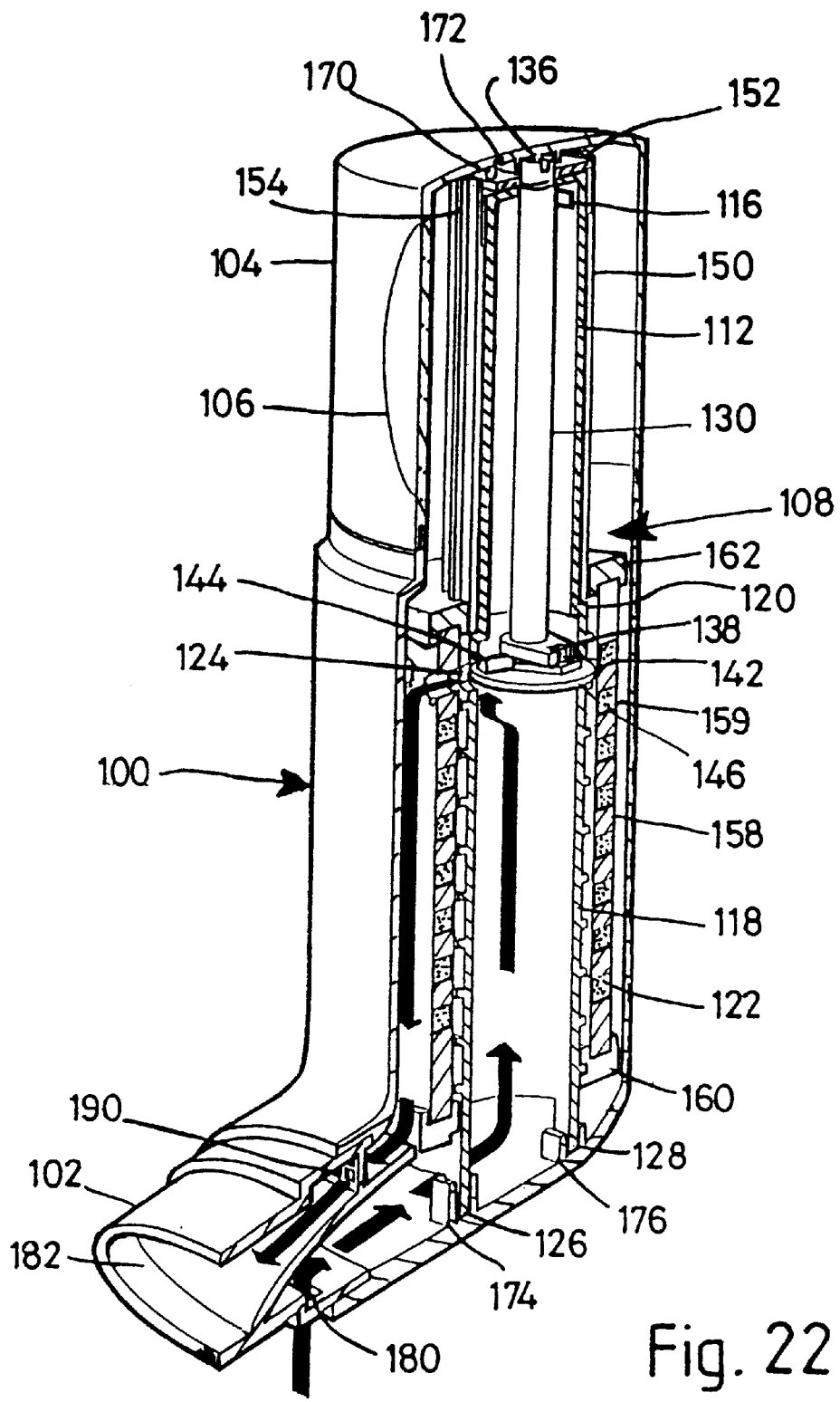
FIG. 22 is a partially cut away isometric view of an inhaler for dispensing doses of powdered medicament from the finished container, which forms part of a cartridge housed in the inhaler.

With reference to FIG. 22, an inhaler in which the container 50 can be used comprises a housing 100 which has a generally cylindrical portion and which is connected at its lower end to a mouth piece 102 extending substantially radially to the main body of the housing 100. The opposite end of the housing 100 includes a rotary member in the form of a cap 104 rotably mounted on the rest of the housing 100. The cap 104 incorporates a window 106 through which a cartridge 108 contained within the body 100 can be viewed.

With reference to FIGS. 23 to 26, the cartridge 108 comprises a hollow cylindrical core 110 which has a reduced diameter upper portion 112 in which there is provided an upper aperture 114 and an integral tang 116. The core 110 also includes a lower portion 118 which is of a larger diameter than the portion 112, and which defines an annular shoulder 120 where it meets the portion 112. The portion 118 includes an external screw thread 122, a radial aperture 124 in its upper region, and two axially extending lower lugs 126 and 128.

The core 110 accommodates a vertical shaft 130, the upper part of which protrudes through the aperture 114. The top of the shaft 130 includes a slot 132 for engaging a protuberance 136 on the underside of the top of the cap 104 so as to provide a rotational key between the shaft 130 and the cap 104. The bottom of the shaft 130 is provided with a radial crank arm 138 which incorporates a radial slot 140 which slidably engages a boss 142 connected to a pin 144 positioned above a plate 146. The pin is in registry with an aperture (not shown) in the case 110 angularly spaced from the aperture 124.

Figure 25:
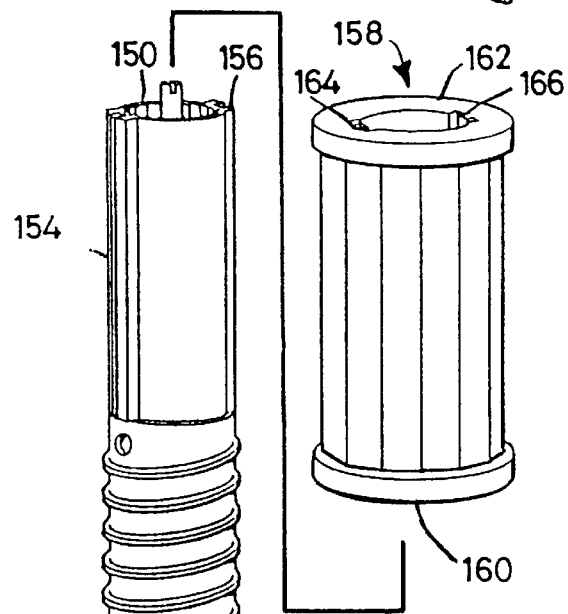
Figure 26:
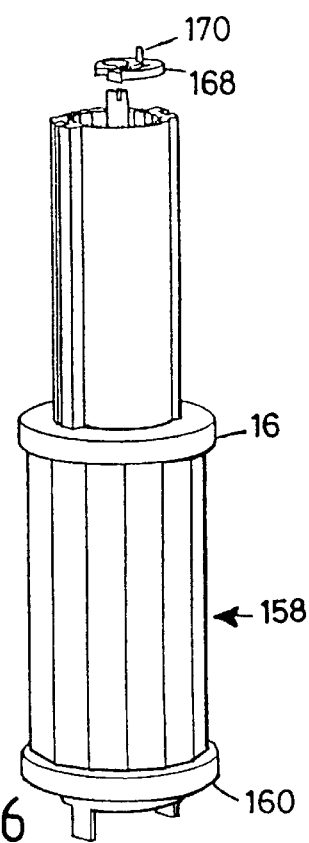
Figure 27:
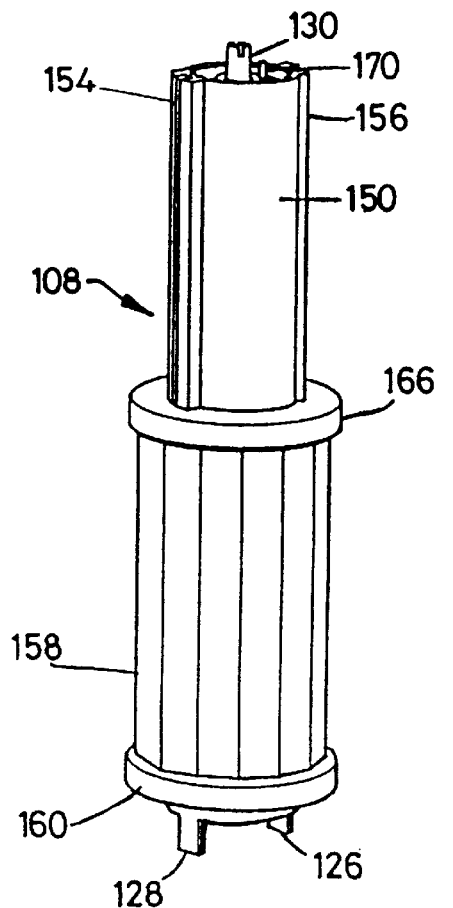
FIG. 27 shows the cartridge when assembled.

The plate 146 is, with the cartridge assembled, attached to the interior of the core by suitable means (not shown), and the pin 144 and plate 146 include guide means (not shown) so arranged that rotation of the shaft 132 causes axial motion of the pin 144. With reference to FIG. 25, the shoulder 120 supports a sleeve 150 which is rotably mounted on the core 110 and which surrounds the upper part 112.

The sleeve 150 includes internal longitudinal serrations 152 and two diametrically opposed sets of external longitudinal ribs 154 and 156.

With reference to FIG. 25, the medicament to be dispensed is contained in a cylindrical container 158 which has side walls which include a number of helically arranged radial through bores such as 159 (FIGS. 5 and 13), each of which contains a respective dose of material. The internal and external surfaces of the side walls are coated with corresponding sheets of a laminated foil which seals both ends of each bore. The container 158 is made by any one of the methods previously described.

The core 110 extends through the centre of the container 158 which includes a lower end cap 160 having a part helical groove (not shown) for engaging the thread 122, and an upper cap 162 which includes two diametrically opposed sets of slots 164 and 166 which engage the sets of ribs 154 and 156 to provide a rotational key between the sleeve 150 and the container 158.

The upper portion of the shaft 130 includes a shoulder 133 which supports a ratchet member 168 which is rotatable with respect to the shaft 130. The ratchet member 168 includes an upper boss 170 which engages in an arcuate track 172 (FIG. 28A) in the underside of the cap 104 to provide a lost motion connection between the cap 104 and the ratchet member 168.

Figure 10:
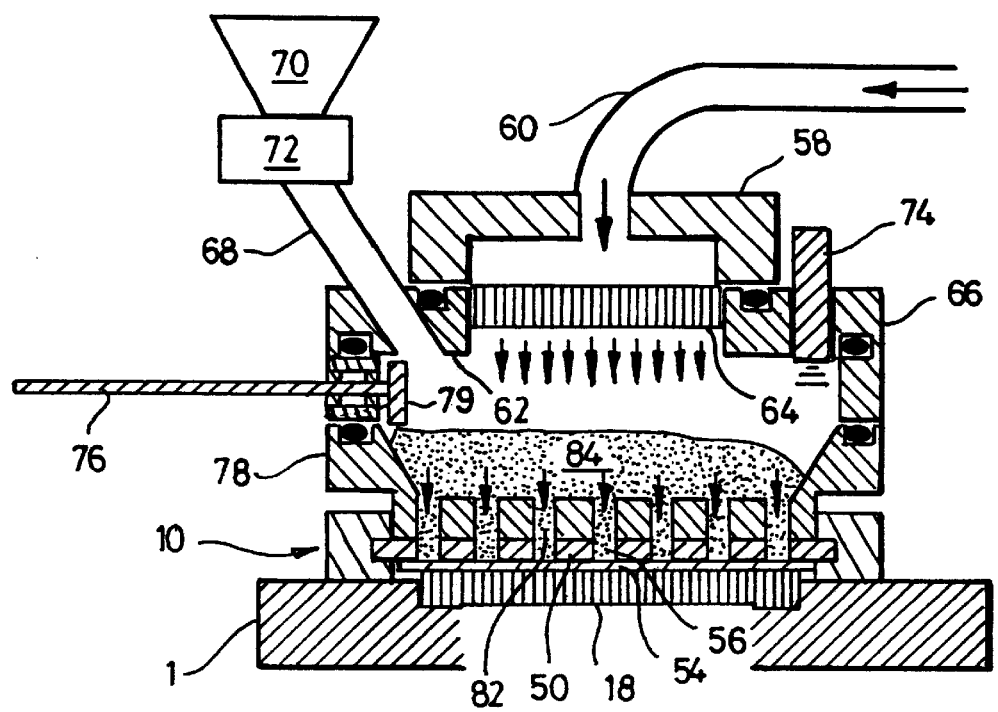
Figure 11:
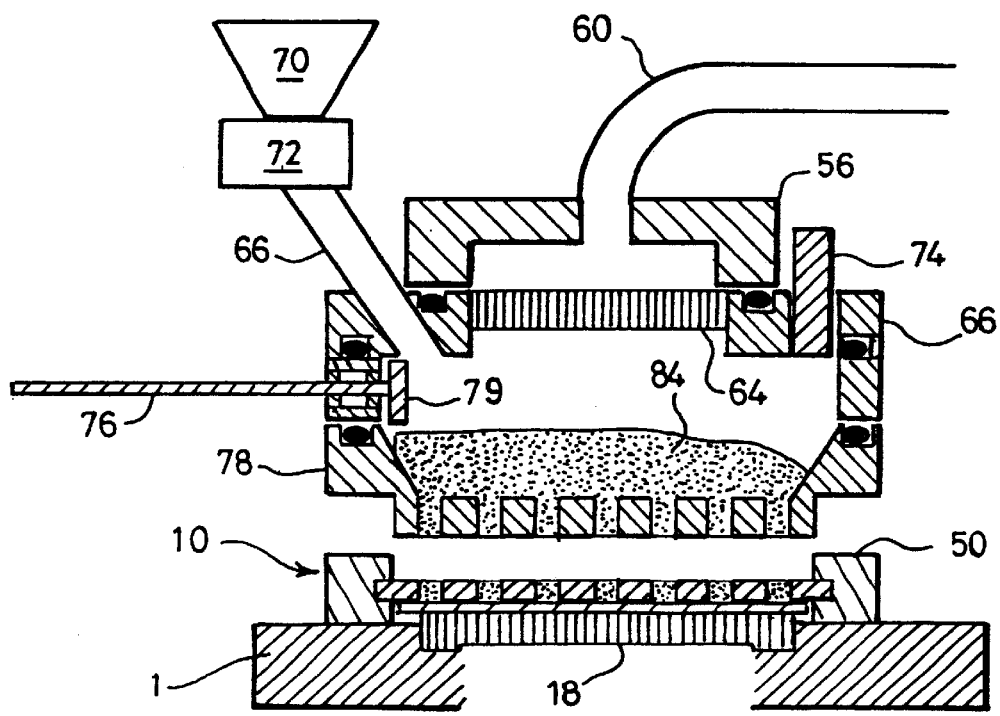
Figure 28:
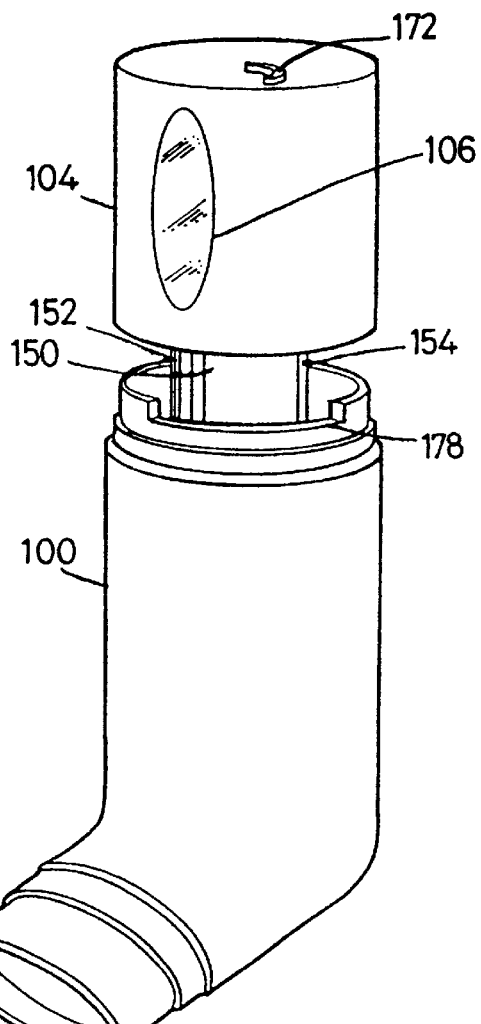
FIG. 28 is a diagrammatic partially exploded view of the cartridge and the housing.

As is illustrated in FIG. 28, the cap 104 is removable from the rest of the housing 100 to enable the assembled cartridge 108 (as shown in FIG. 10) to be inserted into the housing 100 until the lower lugs 126 and 128 of the core 110 engage in corresponding sockets 174, 176 (FIG. 23) in the bottom of the housing 100 to provide a rotational key between the core 110 and the housing 100.

As is illustrated in FIG. 28, the housing 100 includes an upper rebate 178 which cooperates with a downwardly projecting lug (not shown) in the cap 104 to provide stops which define the limits of allowable rotational movement of the cap 104 relative to the rest of the housing 100.

The lugs 126 and 128 space the lower end of the core 110 from the housing 100, thereby enabling the interior of the core 110 to communicate with an air inlet 180 provided in the underside of the mouthpiece 102, which includes an air outlet 182 partitioned from the inlet 180. The container 158 is spaced from the housing 100 so as to provide an outlet passage between vertical inner ribs 182 and 184 (FIG. 29A) which communicates with the outlet 182.

Thus the inhaler includes an airway, indicated by the marked arrows, extending from the air inlet 180 up through the core 110, through the aperture 124 and a dose containing through-bore in registry therewith and then through the outlet passage down to the outlet 182. In order to take a dose of medicament from the inhaler, the user must rotate the cap 104 from one to the other of its end positions and back again, causing the pin 144 to rupture the foil seal for a through bore and causing the through bore subsequently to be moved into registry with the outlet passage. This operation will now be described in greater detail with reference to FIGS. 29A–29F, and FIGS. 30A–30F.

Figure 30A:
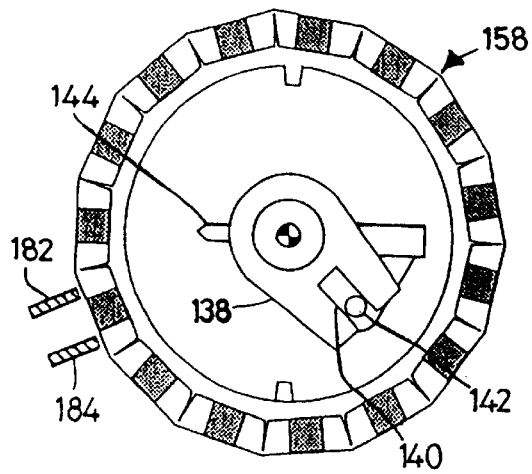
FIGS. 30A–30F are sectional views illustrating the operation of other parts of the device at corresponding stages in the operating cycle thereof.
Figure 30B:
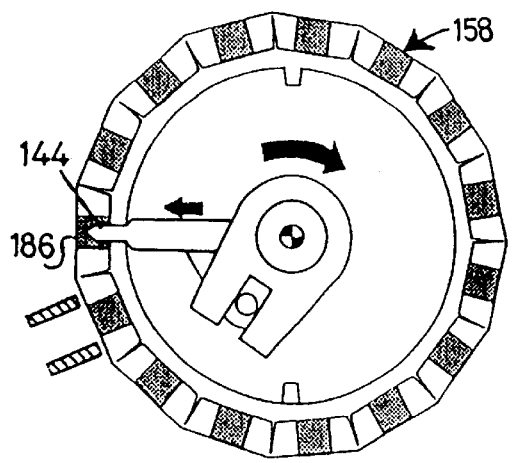
Figure 30C:
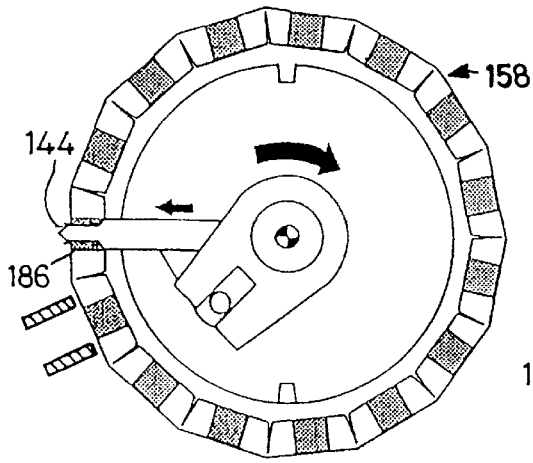
Figure 30D:
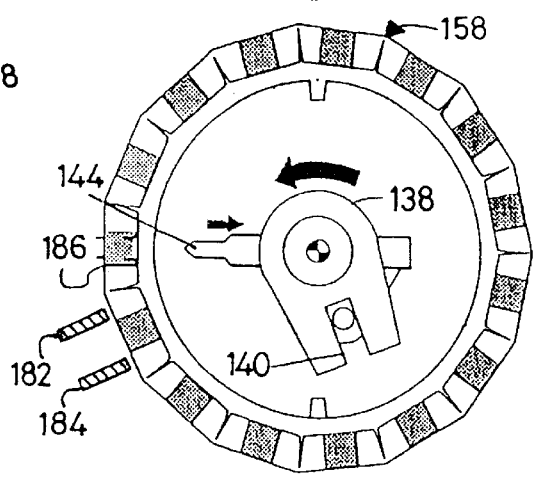
Figure 30E:
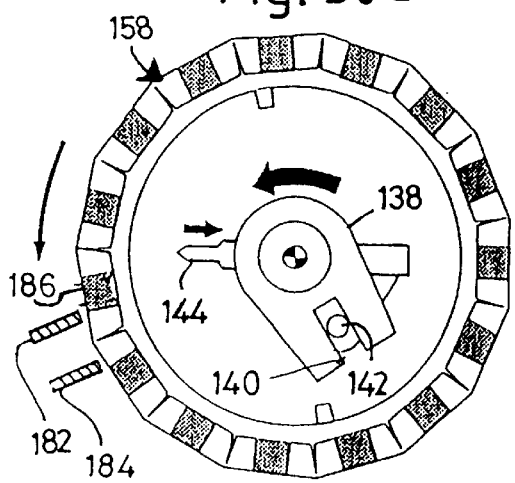

FIG. 29A shows the dispenser in a initial condition in which the pin 144 is retracted and all the compartments are sealed. Rotation of the knob 104 in a clockwise direction as indicated by the arrow 184 of FIG. 29B causes a corresponding rotation of the shaft 130 which, in turn, rotates the crank arm 138 so as to extend the pin 144 until it penetrates the inner seal of a cavity 186 (FIG. 30B). During this process, the slot 172 travels relative to the pin 170 so as to prevent rotation of the ratchet member 168 until the pin 170 engages the trailing end of the slot 172. Further rotation of the knob 104 in the same direction then also causes a corresponding rotation of the member 168 which can rotate relative to the sleeve 150 in a clockwise direction only. As this happens, the engagement of the tang 116 with the serrated inner edge of the sleeve 150 prevents the latter from rotating in an anticlockwise direction. When the limit of allowable clockwise rotation is reached, the member 168 is in the position shown in FIG. 29C and the pin 144 is in the position shown in FIG. 30C in which it extends through and beyond the bore 186 so as to pierce both inner and outer seals.

Figure 30F:
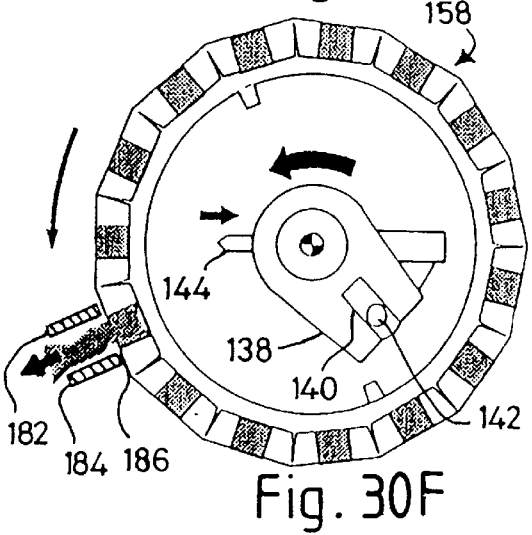

The knob 104 is then rotated in the opposite direction as shown in FIG. 12d, causing the pin 144 to be withdrawn from the bore 186. During the withdrawal of the pin 144, the slot 172 moves relative to the boss 170 so as to prevent corresponding movement of the sleeve 150 (and hence the container 158) until the pin 144 has been fully withdrawn. Further anticlockwise rotation of the knob 104 rotates the member 168, through the engagement of the boss 117 slot 172, in turn causing rotation of the sleeve 150. Since the latter is rotationally keyed to the container 158, this movement causes the container 158 to rotate on the lower portion 118 of the core 110, which in turn moves the through bores including the bore 186 along a part helical path as a result of the engagement of the cap 160 with the screw thread 122. By the time the knob 104 has reached the limit of allowable anticlockwise rotation, as illustrated in FIG. 29F, the bore 186 is in registry with the outlet passage (FIG. 30F).

If the user then inhales through the outlet 182 of the mouthpiece 102, the consequent airflow through the device expels medicament from the bore 186, in to the outlet chamber and out through the outlet 182.

Figure 23:
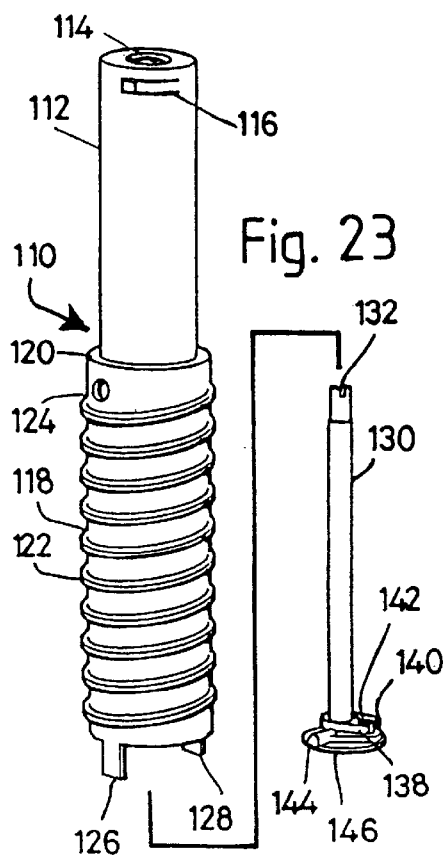
FIGS. 23–26 are exploded isometric views of various components of the cartridge.
Figure 24:
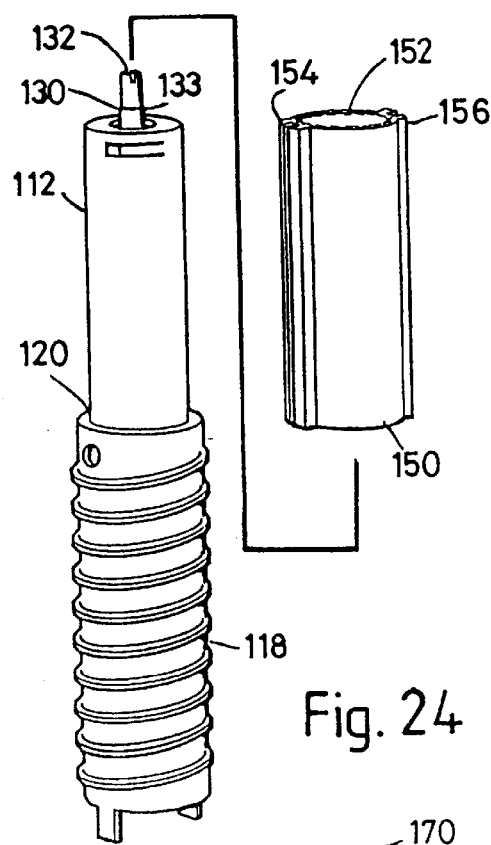

With reference to FIG. 23, the mouthpiece 102 also includes a grille 190 for capturing any loose fragments of the sealing foil which come adrift during inhalation.

The pin 144 is of the kind shown in FIGS. 31 and 32, and is so shaped as to create flaps in the foil seals whilst minimising the amount of material ejected from compartments during insertion. Those flaps are able to move, to allow material to be discharged, but are connected to the rest of the foil so as to reduce the chances of foil fragments breaking free during inhalation.

An alternative type of container for powdered medicament is shown in FIG. 33, and comprises a single rigid plate 350 having a central line of ten apertures such as the aperture 352, each of which contains a respective dose of medicament. The apertures are sealed by two strips of foil, one of which is denoted by reference 354 which extend along opposite of the plate 350. The medicament containing holes are flanked by two 356 and 358 of further holes which help to locate the plate 350 in use.

The central holes in the plate 350 can be filled by the apparatus shown in FIGS. 3–21, when modified so that the number and position of holes in the hopper at the filling station correspond to the number and position of holes in the central line in the container 350. The modified apparatus lacks the rolling station 9 of the previously described apparatus.

What is claimed is:

1. A method of loading a plurality of doses of a predetermined amount of particulate material into a plate having means defining a plurality of apertures extending through the plate, the method comprising the steps of:

A. supporting the plate on a porous bed in such a position that the apertures communicate with a reservoir of an excess amount of particulate material;

B. exerting sufficient gaseous pressure on the material in the reservoir to cause the material to enter and fill the apertures, the porous bed allowing gas to exit the apertures while preventing particulate material from being expelled through the apertures; and C. separating the filled apertures from the reservoir, wherein each dose is contained in a respective aperture, and the volume of each aperture determines the quantity of dose contained therein.

2. A method according to claim 1 in which the particulate material is a powdered medicament which is to be administered by inhalation.

3. A method according to claim 1 in which the apertures are brought into a position in which they simultaneously communicate with a common reservoir, prior to filling.

4. A method according to claim 1 in which the bed comprises a perforated baseplate, having a sheet of finely porous material thereon, the sheet being discarded after use.

5. A method according to claim 1 in which the apertures, once filled, are sealed so that each dose is individually encapsulated in its respective compartment.

6. A method according to claim 5 in which said sealing is achieved by bonding sheet material to each face of the plate.

7. A method according to claim 1 in which the plate is flexible and, after filling, is rolled or otherwise formed into a cylinder.

8. A method according to claim 1 in which the reservoir is contained in a hopper having an array of outlet holes each of which is in registry with a respective aperture, and said gas is supplied to the hopper under sufficient pressure for particulate material to be forced through the outlet holes into the apertures.

9. A method according to claim 8 in which the outlet hole dimensions are selected so as to substantially prevent particulate material from passing therethrough except when forced by gaseous pressure.

10. Apparatus for performing a method according to claim 1, the apparatus comprising a bed of porous material on which the plate can be laid out flat, a filling head for supplying particulate material to the upper surface of the plate, and means for passing air or a gas through the bed and the apertures in the plate to force particulate material into said apertures.

11. Apparatus according to claim 10 in which the filling head comprises a hopper having a series of outlet holes, the relative positions of which correspond to those of the apertures in the plate so that, with the plate in position under the hopper, each outlet hole is in registry with a respective aperture.

12. Apparatus according to claim 11 in which the apparatus includes level detection means for determining the level of particulate material remaining in the hopper, and supply means for supplying further particulate material thereto.

13. Apparatus according to claim 12 in which the hopper is elongate and the level detection means and supply means are so arranged that material is supplied at one end of the hopper and the level of material is detected at a remote region of the hopper, the apparatus further including means for distributing particulate material within the hopper, to achieve a substantially uniform depth therein.

\* \* \* \* \*